United States Patent
Isaza

(10) Patent No.: US 10,744,285 B2
(45) Date of Patent: Aug. 18, 2020

(54) SYSTEMS AND METHODS FOR DETECTION OF VENTILATOR AND PATIENT DISCONNECTIONS USING PATIENT LUNG COMPLIANCE ESTIMATED ON BOTH INHALATION AND EXHALATION PHASES OF A BREATH

(71) Applicant: KONINKLIJKE PHILIPS N.V., Eindhoven (NL)

(72) Inventor: Fernando Jose Isaza, Carlsbad, CA (US)

(73) Assignee: Koninklijke Philips N.V., Eindhoven (NL)

( * ) Notice: Subject to any disclaimer, the term of this patent is extended or adjusted under 35 U.S.C. 154(b) by 277 days.

(21) Appl. No.: 15/538,259

(22) PCT Filed: Dec. 17, 2015

(86) PCT No.: PCT/IB2015/059706
§ 371 (c)(1),
(2) Date: Jun. 21, 2017

(87) PCT Pub. No.: WO2016/103122
PCT Pub. Date: Jun. 30, 2016

(65) Prior Publication Data
US 2018/0015244 A1  Jan. 18, 2018

Related U.S. Application Data

(60) Provisional application No. 62/096,622, filed on Dec. 24, 2014.

(51) Int. Cl.
A61M 16/00 (2006.01)
A61M 16/08 (2006.01)
A61M 39/10 (2006.01)

(52) U.S. Cl.
CPC .... A61M 16/0051 (2013.01); A61M 16/0057 (2013.01); A61M 16/024 (2017.08);
(Continued)

(58) Field of Classification Search
CPC ...... A61M 2205/14; A61M 2039/1005; A61M 2230/46; A61M 16/00; A61M 16/0015;
(Continued)

(56) References Cited

U.S. PATENT DOCUMENTS 4,316,182 A 2/1982 Hodgson
5,881,717 A 3/1999 Isaza
(Continued)

FOREIGN PATENT DOCUMENTS

| WO | 0204057 A1 | 1/2002 |
| WO | 2008033730 A2 | 3/2008 |
| WO | 2009123973 A1 | 10/2009 |
| WO | 2009123974 A1 | 10/2009 |

Primary Examiner — Bradley H Philips
Assistant Examiner — Savannah L Gabriel
(74) Attorney, Agent, or Firm — Daniel H. Brean

(57) ABSTRACT

The system, method and computer-readable storage medium are for detection of ventilator and patient disconnections using patient lung compliance estimated on both inhalation and exhalation phases of a breath. A ventilator breathing system (10) provides breathing gas to a patient, and includes a gas supply (12), a patient tubing circuit (14) coupled to the gas supply, and a gas monitoring system (16, 18) associated with the patient tubing circuit and configured to monitor at least flow and pressure. A control unit (20) is coupled to the monitoring system and configured to determine a patient disconnection from the system by estimating a patient lung compliance ratio based upon determined volumes of gas delivered during the inhalation phase of the breath cycle and exiting during the exhalation phase of the breath cycle, and monitored pressures in the patient tubing circuit during the inhalation and exhalation phases of the breath cycle.

15 Claims, 2 Drawing Sheets

(52) U.S. Cl.
CPC ...... *A61M 16/026* (2017.08); *A61M 16/0833* (2014.02); *A61M 16/0883* (2014.02); *A61M 2016/0021* (2013.01); *A61M 2016/0027* (2013.01); *A61M 2016/0036* (2013.01); *A61M 2016/0039* (2013.01); *A61M 2016/0042* (2013.01); *A61M 2039/1005* (2013.01); *A61M 2205/13* (2013.01); *A61M 2205/14* (2013.01); *A61M 2205/18* (2013.01); *A61M 2205/3331* (2013.01); *A61M 2205/3334* (2013.01); *A61M 2205/502* (2013.01); *A61M 2230/46* (2013.01)

(58) Field of Classification Search
CPC ............ A61M 16/0018; A61M 16/021; A61M 16/22; A61M 16/024; A61B 5/00
See application file for complete search history.

(56) References Cited

U.S. PATENT DOCUMENTS

| | | | |
|---|---|---|---|
| 6,142,150 A * | 11/2000 | O'Mahoney | A61M 16/0072 128/204.18 |
| 6,668,824 B1 | 12/2003 | Isaza et al. | |
| 2006/0086357 A1* | 4/2006 | Soliman | A61M 16/0051 128/204.22 |
| 2008/0053441 A1 | 3/2008 | Gottlib et al. | |
| 2011/0277758 A1 | 11/2011 | Dixon et al. | |
| 2011/0282228 A1* | 11/2011 | Shiner | A61B 5/085 600/534 |
| 2012/0137249 A1 | 5/2012 | Milne et al. | |
| 2012/0216809 A1 | 8/2012 | Milne et al. | |
| 2012/0272962 A1 | 11/2012 | Doyle et al. | |
| 2014/0005566 A1 | 1/2014 | Homuth et al. | |
| 2014/0034054 A1 | 2/2014 | Angelico et al. | |

* cited by examiner

SYSTEMS AND METHODS FOR DETECTION OF VENTILATOR AND PATIENT DISCONNECTIONS USING PATIENT LUNG COMPLIANCE ESTIMATED ON BOTH INHALATION AND EXHALATION PHASES OF A BREATH

CROSS-REFERENCE TO PRIOR APPLICATIONS

This application is the U.S. National Phase application under 35 U.S.C. § 371 of International Application No. PCT/IB2015/059706, filed on Dec. 17, 2015, which claims the benefit of U.S. Provisional Patent Application No. 62/096,622, filed on Dec. 24, 2014. These applications are hereby incorporated by reference herein.

TECHNICAL FIELD

The invention relates to the field of ventilators, in particular to a method and apparatus for controlling a ventilation therapy device including the detection of a disconnection using estimated patient lung compliance.

BACKGROUND

A patient receiving breath pressure support from a ventilator system typically receives breathing gas through a patient circuit of the ventilator. The patient circuit generally includes two conduits (e.g. flexible tubing) connected to a fitting referred to as a tubing circuit wye. The free ends of the conduits are attached to the ventilator so that one conduit receives breathing gas from the ventilator's pneumatic system, and the other conduit returns gas exhaled by the patient to the ventilator. The volume of the exhaled gas may then be measured before it finally exits through an exhalation valve. The wye fitting is typically connected to the patient's breathing attachment or enclosure, which conducts breathing gas into the lungs, and exhaled gas from the lungs to the exhalation branch of the patient circuit. The pneumatic system at the inhalation end of the patient circuit is typically closed before a breath, and the exhalation valve at the exhalation end of the patient circuit is typically preceded by a one-way valve, to prevent gas from flowing in the exhalation branch of the patient circuit.

During ventilation of a patient, it may be important to monitor the state of the gas path ways as these are the conduits of the gases delivered to and received from the patient. The flow of the therapeutic gases to and from the patient can be interrupted via different mechanisms, some related to the valves in the system or by blockage of the tubing system or by disconnections of the gas path way at any of the Ventilator's Breathing System (VBS) elements' interconnection points. In particular, the disconnection type of gas flow interruption is what ventilator designers refer to as "tubing circuit disconnection".

Disconnections in the VBS are common occurrence during ventilation of patients. They can be caused by involuntary actions of the patient or the caregivers or the deliberate action of the care giver such as when suctioning of the patient airways is performed. When a VBS disconnection occurs, gas delivery to the patient is impaired and protection for the caregiver from airborne pathogens is usually impaired as well. Some disconnection episodes are more severe than others in particular when an accidental disconnection occurs (typically caused by involuntary patient action) and is not promptly identified by the ventilator thus the proper alarm is not issued, causing the patient to lack adequate ventilation from being delivered to his/her lungs. Disconnections can occur at several places in the VBS. A typical disconnection is that in which the patient's endotracheal tube (ET) or tracheotomy tube is separated from the tubing system patient port. Another type of disconnection is that that occurs when the tubing system is separated from the ventilator's exhalation port inlet. Furthermore, disconnections may occur at the water traps' or bacteria filter's connection ports or the humidifier etc. Also, the patient may become disconnected from his/her endotracheal tube or tracheotomy tube, which is typically referred to as extubation.

There may be a number of approaches, which are based on identification of conditions, particular to the pressures, delivered and exhaled flows and volumes that exist during a Ventilator's Breathing System disconnection episode. These approaches typically include a set of conditions for the system pressures and or flows and or volumes. In particular, in various known approaches, the pressure and flow criteria need to be chosen based on experimental data which is machine dependent. Such approaches are complex and require the determination of thresholds which can be machine dependent. Review of clinical literature with respect to this issue will readily indicate the frequency and potential hazard to the patient created by disconnections and their affect on the patient when not detected or when the approaches used are flawed or take a significant amount of time to detect these events.

Accordingly, it may be desired to provide for the reliable machine-independent approach for determination of patient disconnection in a ventilation breathing system.

SUMMARY

Embodiments of the invention may provide an apparatus, systems, methods, and computer-readable storage medium for detection of ventilator and patient disconnections using patient lung compliance estimated on both inhalation and exhalation phases of a breath. An embodiment that may achieve this is directed to a ventilator breathing system (VBS) to provide breathing gas to a patient, and having a breath cycle including an inhalation phase and an exhalation phase. The VBS includes a gas supply, a patient tubing circuit coupled to the gas supply, and a gas monitoring system associated with the patient tubing circuit and configured to monitored at least volume and pressure. A control unit is coupled to the monitoring system and configured to determine a patient disconnection from the VBS by estimating a patient lung compliance ratio based upon determined volumes of gas delivered during the inhalation phase of the breath cycle and exiting during the exhalation phase of the breath cycle, and monitored pressures in the patient tubing circuit during the inhalation and exhalation phases of the breath cycle.

It may be noted that the inhalation and exhalation phases are determined by the ventilator. These phases are different from the "physiological" inhalation and exhalation phases which are dependent upon the patient and are identified by the magnitude of the lung flow and the time at which the magnitude is zero.

In an embodiment, the patient tubing circuit may include a patient interface, an inspiratory branch and an expiratory branch each in fluid communication with each other via a tubing circuit wye, and wherein a plurality of sensors of the gas monitoring system comprise one or more inspiratory branch sensors and one or more expiratory branch sensors.

In an embodiment, the gas supply may include a pump and reservoir.

In an embodiment, the control unit is configured to estimate the patient lung compliance ratio by estimating an inhalation patient lung compliance during the inhalation phase of the breath cycle, and estimating an exhalation patient lung compliance during the exhalation phase of the breath cycle.

In an embodiment, the control unit is configured to estimate inhalation patient lung compliance based upon the determined volume of gas delivered during the inhalation phase of the breath cycle, a monitored pressure of gas in the patient tubing circuit at a beginning of the inhalation phase and a monitored pressure of gas in the patient tubing circuit at an end of the inhalation phase.

In an embodiment, the control unit is configured to estimate exhalation patient lung compliance based upon the determined volume of gas exited during the exhalation phase of the breath cycle, a monitored pressure of gas in the patient tubing circuit at an end of the exhalation phase and the monitored pressure of gas in the patient tubing circuit at the end of the inhalation phase.

In an embodiment, the control unit is configured to determine the patient disconnection from the VBS by comparing the estimated patient lung compliance ratio to a threshold.

In an embodiment, the control unit is configured to estimate the patient lung compliance ratio by estimating an inhalation patient lung compliance during the inhalation phase of the breath cycle, and estimating an exhalation patient lung compliance during the exhalation phase of the breath cycle; wherein the patient lung compliance ratio=$(C_{inh}/C_{exh})$; $C_{inh}$ is the inhalation patient lung compliance estimated during the inhalation phase and is calculated as $C_{inh}=V_{inh}/(P_{eoi}-P_{boi})$; $C_{exh}$ is the exhalation patient lung compliance estimated during the exhalation phase and is calculated as $C_{exh}=V_{exh}/(P_{eoi}-P_{eoe})$; wherein $V_{inh}$=the volume of gas delivered during the inhalation phase, $V_{exh}$=the volume of gas exiting during the exhalation phase, $P_{boi}$=pressure monitored in the patient tubing circuit at the beginning of the inhalation phase, $P_{eoi}$=pressure monitored in the patient tubing circuit at the end of the inhalation phase, $P_{eoe}$=pressure monitored in the patient tubing circuit at the end of the exhalation phase; and wherein the control unit is configured to determine the patient disconnection from the VBS by comparing the estimated patient lung compliance ratio to a threshold.

Embodiments of the invention are also directed to a method of determining a patient disconnection from a ventilator breathing system (VBS) configured to provide breathing gas to a patient via a patient tubing circuit and having a breath cycle including an inhalation phase and an exhalation phase. The method includes: monitoring at least flow and pressure of gas in the patient tubing circuit; estimating a patient lung compliance ratio based upon determined volumes of gas delivered during the inhalation phase of the breath cycle and exiting during the exhalation phase of the breath cycle, and monitored pressures in the patient tubing circuit during the inhalation and exhalation phases of the breath cycle; and determining patient disconnect by comparing the estimated patient lung compliance ratio to a threshold.

In an embodiment, the patient tubing circuit includes a patient interface, an inspiratory branch and an expiratory branch each in fluid communication with each other via a tubing circuit wye; and wherein monitoring comprises processing signals from a plurality of sensors in the inspiratory branch and expiratory branch.

In an embodiment, estimating the patient lung compliance ratio comprises estimating an inhalation patient lung compliance during the inhalation phase of the breath cycle, and estimating an exhalation patient lung compliance during the exhalation phase of the breath cycle.

In an embodiment, the estimating of the inhalation patient lung compliance is based upon the determined volume of gas delivered during the inhalation phase of the breath cycle, a monitored pressure of gas in the patient tubing circuit at a beginning of the inhalation phase and a monitored pressure of gas in the patient tubing circuit at an end of the inhalation phase.

In an embodiment, the estimating of the exhalation patient lung compliance is based upon the determined volume of gas exited during the exhalation phase of the breath cycle, a monitored pressure of gas in the patient tubing circuit at an end of the exhalation phase and the monitored pressure of gas in the patient tubing circuit at the end of the inhalation phase.

In an embodiment, estimating the patient lung compliance ratio comprises estimating an inhalation patient lung compliance during the inhalation phase of the breath cycle, and estimating an exhalation patient lung compliance during the exhalation phase of the breath cycle; wherein the patient lung compliance ratio=$(C_{inh}/C_{exh})$; $C_{inh}$ is the inhalation patient lung compliance estimated during the inhalation phase and is calculated as $C_{inh}=V_{inh}/(P_{eoi}-P_{boi})$; $C_{exh}$ is the exhalation patient lung compliance estimated during the exhalation phase and is calculated as $C_{exh}=V_{exh}/(P_{eoi}-P_{eoe})$; wherein $V_{inh}$=the volume of gas delivered during the inhalation phase, $V_{exh}$=the volume of gas exiting during the exhalation phase, $P_{boi}$=pressure monitored in the patient tubing circuit at the beginning of the inhalation phase, $P_{eoi}$=pressure monitored in the patient tubing circuit at the end of the inhalation phase, $P_{eoe}$=pressure monitored in the patient tubing circuit at the end of the exhalation phase.

Embodiments of the invention may also be directed to a non-transitory computer-readable storage medium having stored therein machine readable instructions configured to be executed by a processor to control a ventilator breathing system (VBS) to provide breathing gas to a patient via a patient tubing circuit and having a breath cycle including an inhalation phase and an exhalation phase, the machine readable instructions being configured to cause the VBS to execute a process to determine a patient disconnection from the VBS including: monitoring at least flow and pressure of gas in the patient tubing circuit; estimating a patient lung compliance ratio based upon determined volumes of gas delivered during the inhalation phase of the breath cycle and exiting during the exhalation phase of the breath cycle, and monitored pressures in the patient tubing circuit during the inhalation and exhalation phases of the breath cycle; and determining patient disconnect by comparing the estimated patient lung compliance ratio to a threshold.

In an embodiment, the patient tubing circuit includes a patient interface, an inspiratory branch and an expiratory branch each in fluid communication with each other via a tubing circuit wye; and wherein monitoring comprises processing signals from a plurality of sensors in the inspiratory branch and expiratory branch.

In an embodiment, estimating the patient lung compliance ratio comprises estimating an inhalation patient lung compliance during the inhalation phase of the breath cycle, and estimating an exhalation patient lung compliance during the exhalation phase of the breath cycle.

In an embodiment, the estimating of the inhalation patient lung compliance is based upon the determined volume of gas delivered during the inhalation phase of the breath cycle, a monitored pressure of gas in the patient tubing circuit at a beginning of the inhalation phase and a monitored pressure of gas in the patient tubing circuit at an end of the inhalation phase.

In an embodiment, the estimating of the exhalation patient lung compliance is based upon the determined volume of gas exited during the exhalation phase of the breath cycle, a monitored pressure of gas in the patient tubing circuit at an end of the exhalation phase and the monitored pressure of gas in the patient tubing circuit at the end of the inhalation phase.

In an embodiment, estimating the patient lung compliance ratio comprises estimating an inhalation patient lung compliance during the inhalation phase of the breath cycle, and estimating an exhalation patient lung compliance during the exhalation phase of the breath cycle; wherein the patient lung compliance ratio=$(C_{inh}/C_{exh})$; $C_{inh}$ is the inhalation patient lung compliance estimated during the inhalation phase and is calculated as $C_{inh}=V_{inh}/(P_{eoi}-P_{boi})$; $C_{exh}$ is the exhalation patient lung compliance estimated during the exhalation phase and is calculated as $C_{exh}=V_{exh}/(P_{eoi}-P_{eoe})$; wherein $V_{inh}$=the volume of gas delivered during the inhalation phase, $V_{exh}$=the volume of gas exiting during the exhalation phase, $P_{boi}$=pressure monitored in the patient tubing circuit at the beginning of the inhalation phase, $P_{eoi}$=pressure monitored in the patient tubing circuit at the end of the inhalation phase, $P_{eoe}$=pressure monitored in the patient tubing circuit at the end of the exhalation phase.

BRIEF DESCRIPTION OF THE DRAWINGS

The present invention will be more readily understood from the detailed description of exemplary embodiments presented below considered in conjunction with the accompanying drawings, as follows.

DETAILED DESCRIPTION

Figure 1:
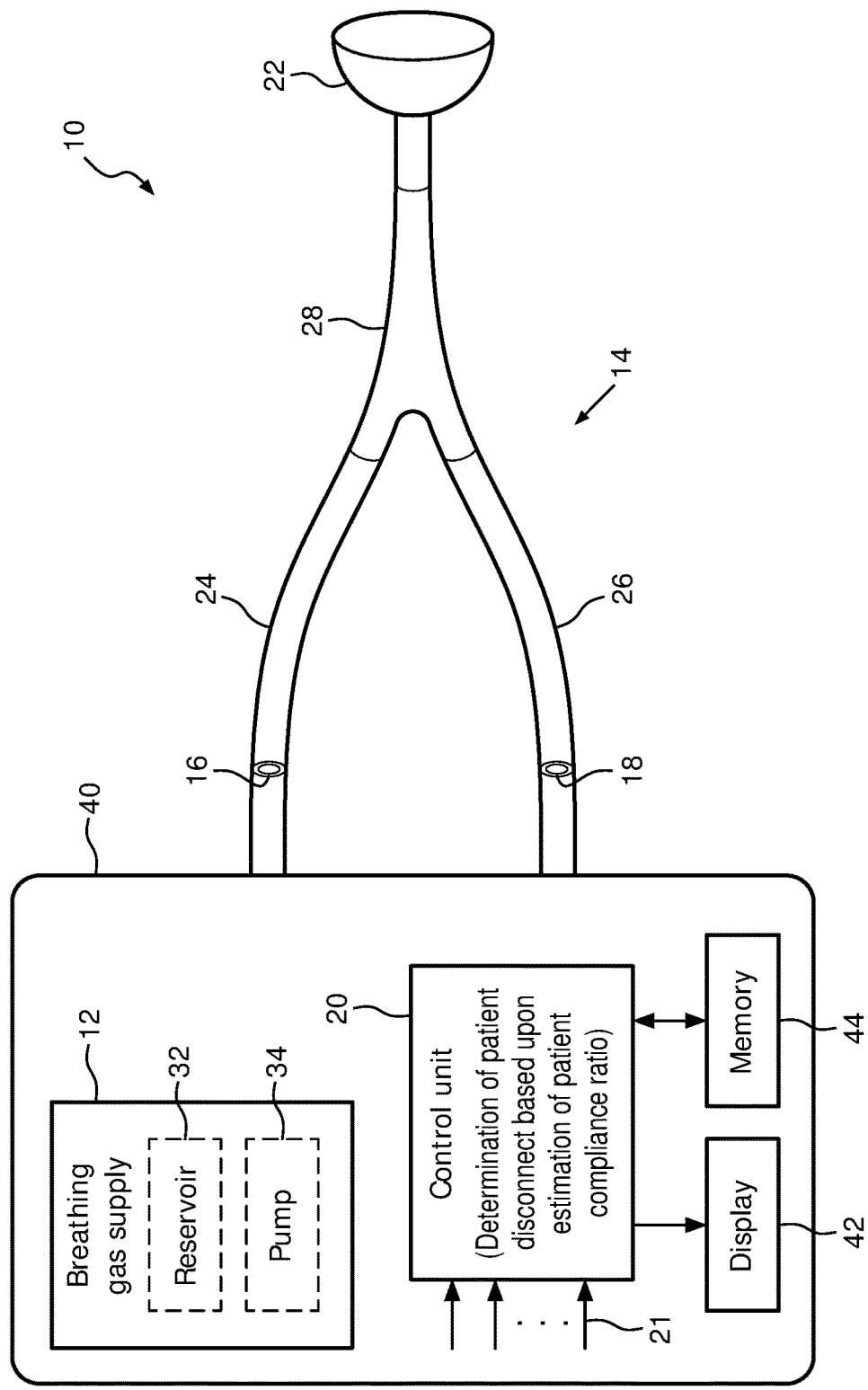
FIG. 1 is a schematic block diagram illustrating a ventilation breathing system including the capability to assess conditions for the determination of patient disconnect in accordance with features of an embodiment of the present invention.

The present invention will now be described more fully hereinafter with reference to the accompanying drawings, in which embodiments of the present invention are shown. The present invention may, however, be embodied in different forms and should not be construed as limited to the embodiments set forth herein. Rather, these embodiments are provided as teaching examples of the invention. Within the present disclosure and claims, when something is said to have "approximately" a certain value, then it means that it is within 10% of that value, and when something is said to have "about" a certain value, then it means that it is within 25% of that value.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Like numbered elements in these figures are either equivalent elements or perform the same function. Elements which have been discussed previously will not necessarily be discussed in later figures if the function is equivalent.

Initially, it is noted that a typical positive pressure ventilator may include a compressible air reservoir, or a turbine, or high pressure air and oxygen sources, a set of valves and tubes, and a patient tubing circuit. The air reservoir is pneumatically compressed several times a minute to deliver room-air, or in most cases, an air/oxygen mixture to the patient. If a turbine is used, the turbine pushes air through the ventilator, with pressure regulation adjusting pressure to meet patient-specific parameters. When overpressure is released, the patient will exhale passively due to the lungs' elasticity, the exhaled air being released usually through a one-way valve within the patient tubing circuit called the patient manifold. The oxygen content of the inspired gas can be set, for example, from 21 percent (ambient air) to 100 percent (pure oxygen). Pressure and flow characteristics can be set mechanically or electronically.

Ventilators may also be equipped with monitoring and alarm systems for patient-related parameters (e.g. pressure, volume, and flow) and ventilator function (e.g. air leakage, power failure, and mechanical failure), backup batteries, oxygen tanks, and remote control. A computer-controlled turbo pump may also be used. Modern ventilators are electronically controlled by a small embedded system to allow exact adaptation of pressure and flow characteristics to an individual patient's needs. Fine-tuned ventilator settings also serve to make ventilation more tolerable and comfortable for the patient. Respiratory therapists may be responsible for tuning these settings while biomedical technologists are responsible for the maintenance.

The patient tubing circuit usually includes a set of three durable, lightweight plastic tubes, separated by function (e.g. inhaled air, patient pressure, exhaled air). Determined by the type of ventilation needed, the patient-end of the circuit may be either noninvasive or invasive. Noninvasive methods, which are adequate for patients who require a ventilator only while sleeping and resting, mainly employ a nasal mask. Invasive methods require intubation, which for long-term ventilator dependence will normally be a tracheotomy cannula, as this is much more comfortable and practical for long-term care than is larynx or nasal intubation.

Referring initially to FIG. 1, a ventilation breathing system 10 in accordance with features of the invention will be described. FIG. 1 schematically illustrates a VBS 10 which may be an electronically controlled ventilation breathing system. The VBS 10 provides breathing gas from a breathing gas supply 12 to a patient. In some embodiments, the breathing gas supply may include a reservoir 32 and pump 34. In operation, the VBS 10 has a breath cycle including an inhalation phase and an exhalation phase. The VBS 10 includes a patient tubing circuit 14 coupled to the breathing gas supply 12, and a gas monitoring system 16/18 associated with the patient tubing circuit 14. As illustrated, the gas monitoring system 16/18 includes, for example, a plurality of sensors positioned to measure at least flow and pressure in the patient tubing circuit 14.

A control unit 20 is coupled to the monitoring system 16/18 and configured to determine a patient disconnection from the VBS 10 by estimating a patient lung compliance ratio based upon determined volumes of gas delivered during the inhalation phase of the breath cycle and exiting during the exhalation phase of the breath cycle, and monitored or measured pressures in the patient tubing circuit 14 during the inhalation and exhalation phases of the breath cycle. A determination of patient disconnection may trigger an alarm, for example, to be output on display 42. Of course audible or other remote transmissions of such alarm are contemplated herein. The control unit 20 may access memory 44 for instructions, as described in more detail below.

The breathing gas supply 12, control unit 20, display 42 and/or memory 44 may be carried in a housing 40, as shown, or may be provided as separate or external components to the VBS 10. Such housing may also include a user interface (e.g. keyboard, touch screen etc. (not shown)) to input commands and/or settings from an operator (e.g. respiratory therapist).

As discussed above, the patient tubing circuit 14 may include a patient interface 22, an inspiratory branch 24 and an expiratory branch 26 each in fluid communication with each other via a tubing circuit wye 28 (or patient wye). As such, the plurality of sensors of the gas monitoring system comprise at least one inspiratory branch sensor 16 and at least one expiratory branch sensor 18. The inspiratory branch sensor 16 and expiratory branch sensor 18 may include a respective transducer, for example, capable of measuring pressure and flow, or may include the use of separate sensors for each of pressure and flow. Of course various other numbers and arrangements of pressure and flow sensors associated with the patient tubing circuit 14 are considered.

The patient is connected to the patient tubing circuit 14 via the patient interface 22 (e.g. to receive breathing gas). Outputs from the sensors 16/18 are received by the control unit 20 (e.g. at inputs 21) which governs processor and/or microcomputer based functions of the VBS 10. Such control unit 20 could of course be a separate component from a primary processor and/or microcomputer of the VBS 10. Although not shown here, the VBS 10 may also include pressure control valves controlling pressure of breathing gas delivered to the patient, and safety valves for relieving excessive pressure of the breathing gas in the patient tubing circuit 14.

The pump 34 (or pressure generator) may be, for example, integrated, combined, coupled, or connected with the breathing gas supply. Respiratory therapy may recommend delivery of a pressurized flow of breathable gas to the airway of a subject, providing one or more inhalation pressure, flow, and/or volume levels during the inhalation phase, and one or more exhalation pressure, flow, and/or volume levels during the exhalation phase. Any pressure level during an inhalation phase may be referred to as an inhalation pressure level, though such a pressure level need not be constant throughout the inhalation phase. The pressure and/or flow levels may be either predetermined or fixed, follow a predetermined dynamic characteristic, or they may dynamically change breath-to-breath or over several breaths.

The patient may or may not initiate one or more phases of respiration. Ventilatory support may be implemented as a higher and lower positive pressure of a (multi-level) PAP device. For example, to support inspiration, the pressure of the pressurized flow of breathable gas may be adjusted to an inspiratory pressure and/or may be adjusted to a flow level. Alternatively, and/or simultaneously, to support expiration, the pressure of the pressurized flow of breathable gas may be adjusted to an expiratory pressure. Other schemes for providing respiratory support (including Volume Control Ventilation (VCV), Pressure Control Ventilation (PCV), Airway Pressure Release Ventilation (APRV), Pressure Regulated Volume Control (PRVC), CPAP, BiPAP®, and/or other schemes) through the delivery of the pressurized flow of breathable gas are contemplated.

The VBS 10 may be configured such that one or more gas parameters of the pressurized flow of breathable gas are controlled in accordance with a therapeutic respiratory regimen for the patient. The one or more gas parameters may include one or more of flow, volume, pressure, humidity, gas mix, velocity, acceleration, gas leak, and/or other parameters. The VBS 10 may be configured to provide types of therapy including types of therapy where a subject performs inspiration and/or expiration of his/her own accord and/or where the device provides mandatory controlled breaths.

The patient tubing circuit 14 may be a conduit such as a single-limb or a dual-limb flexible length of hose, or other conduit, that places the patient interface 22 in fluid communication with the breathing gas supply 12. The patient tubing circuit 14 forms a flow path through which the pressurized flow of breathable gas is communicated between the breathing gas supply 12 and the patient interface 22.

The patient interface 22 of VBS 10 in FIG. 1 is configured to deliver the pressurized flow of breathable gas to the airway of a patient. As such, the patient interface 22 may include any appliance suitable for this function. In certain embodiments, the patient interface 22 is configured to be removably coupled with another interface appliance being used to deliver respiratory therapy to the patient. For example, the patient interface 22 may be configured to engage with and/or be inserted into an endotracheal tube, a tracheotomy portal, and/or other interface appliance. In certain embodiments, the patient interface 22 may be configured to engage the airway of the patient without an intervening appliance. In such embodiment, the patient interface 22 may include one or more of an endotracheal tube, a tracheotomy tube, a nasal mask, a nasal/oral mask, a full face mask, a total face mask, a partial rebreathing mask, or other interface appliance that bi-directionally communicates a flow of gas with an airway of a patient. The present disclosure is not limited to these examples, and contemplates delivery of the pressurized flow of breathable gas to a patient using other patient interfaces.

The present approach compares the patient's lung compliance estimated during the inhalation phase of a breath with the lung compliance estimated during the exhalation phase of the same breath. This comparison is done by computing the ratio between the two compliances and the result is compared to a pre-determined threshold. The threshold used is such that it represents the possible disconnection types that can occur during ventilation of a patient. The type of ventilation modalities for which this approach is relevant include, for example, invasive ventilation and non-invasive ventilation. The accuracy in the estimates of compliance may not be significant because the same level of inaccuracy will be present in the estimation of the inhalation compliance and the exhalation compliance estimates. Furthermore, since the criteria may be based on the ratio of the two estimates, the inaccuracies tend to cancel each other out.

It should be noted that this is a consequence of the use of the same pressure sensors for both estimations and typically similar delivery and exhalation flow sensor accuracies. It may be understood that the compliance ratio can be tailored based on the differences in the accuracies of the flow and pressure sensors, if needed.

The test of the following inequality may be used as the criteria for the detection of the disconnection events: Ratio≤Threshold; where Ratio=$(C_{inh}/C_{exh})$.

The Patient Lung Compliance estimated during the inhalation phase of a breath ($C_{inh}$) may be calculated using the following equation: $C_{inh}=V_{inh}/(P_{eoi}-P_{boi})$. The Patient Lung Compliance estimated during the exhalation phase of a breath ($C_{exh}$) may be calculated using the following equation: $C_{exh}=V_{exh}/(P_{eoi}-P_{eoe})$; where $V_{inh}$=Volume of the gas delivered by the ventilator during the inhalation phase of a breath; $V_{exh}$=Volume of the gas leaving the ventilator during the exhalation phase of a breath; $P_{boi}$=Pressure monitored in the patient tubing circuit system at the beginning of the inhalation phase of a breath; $P_{eoi}$=Pressure monitored in the patient tubing circuit system at the end of the inhalation phase of a breath; $P_{eoe}$=Pressure monitored in the patient tubing circuit system at the end of the exhalation phase of a breath; and the threshold=typically a low value such as 0.1. Of course other values may be determined as needed.

Specifically, when the inequality is true, the patient tubing circuit 14 is considered disconnected: a) from the patient, which includes extubation; or b) due to a separation of the patient tubing circuit 14 at one or various interconnection places within itself, which includes separation for the VBS 10 at the patient tubing circuit 14 connection ports.

It should be noted that the compliances estimated using the equations above may be referred to as apparent compliances because the pressure measurements may not represent the pressure at the patient lungs since they are measurements of the pressure in the patient tubing circuit 14 which, under non-zero lung flow conditions, may differ significantly from the pressure at the lung. It is noted that this is caused by calculation of the compliances at the point where the ventilator decides to consider the beginning or end of the phases based on criteria other than the zero flow criterion that is characteristic of the physiological phases of a breath. The present disconnection detection approach may include the characteristic of being able to detect disconnections of the patient tubing circuit 14 at any of its junctions or connections to the VBS 10, as well as disconnections of the ET tube and extubation of the patient while an external sensing apparatus (such as the NME CO2 and flow sensor) are still attached to the patient tubing circuit wye 28.

The approach of the present embodiments utilizes the information needed for detection of disconnections of the Ventilator Breathing System elements in a compact and efficient manner, since the approach is based on the estimation of the patient's lung compliance, which includes the use of delivered and exhaled volumes as well as the pressure levels present in the system during ventilation. Furthermore, the approach is machine independent as it may only rely on the patient's lung compliance characteristics.

Figure 2:
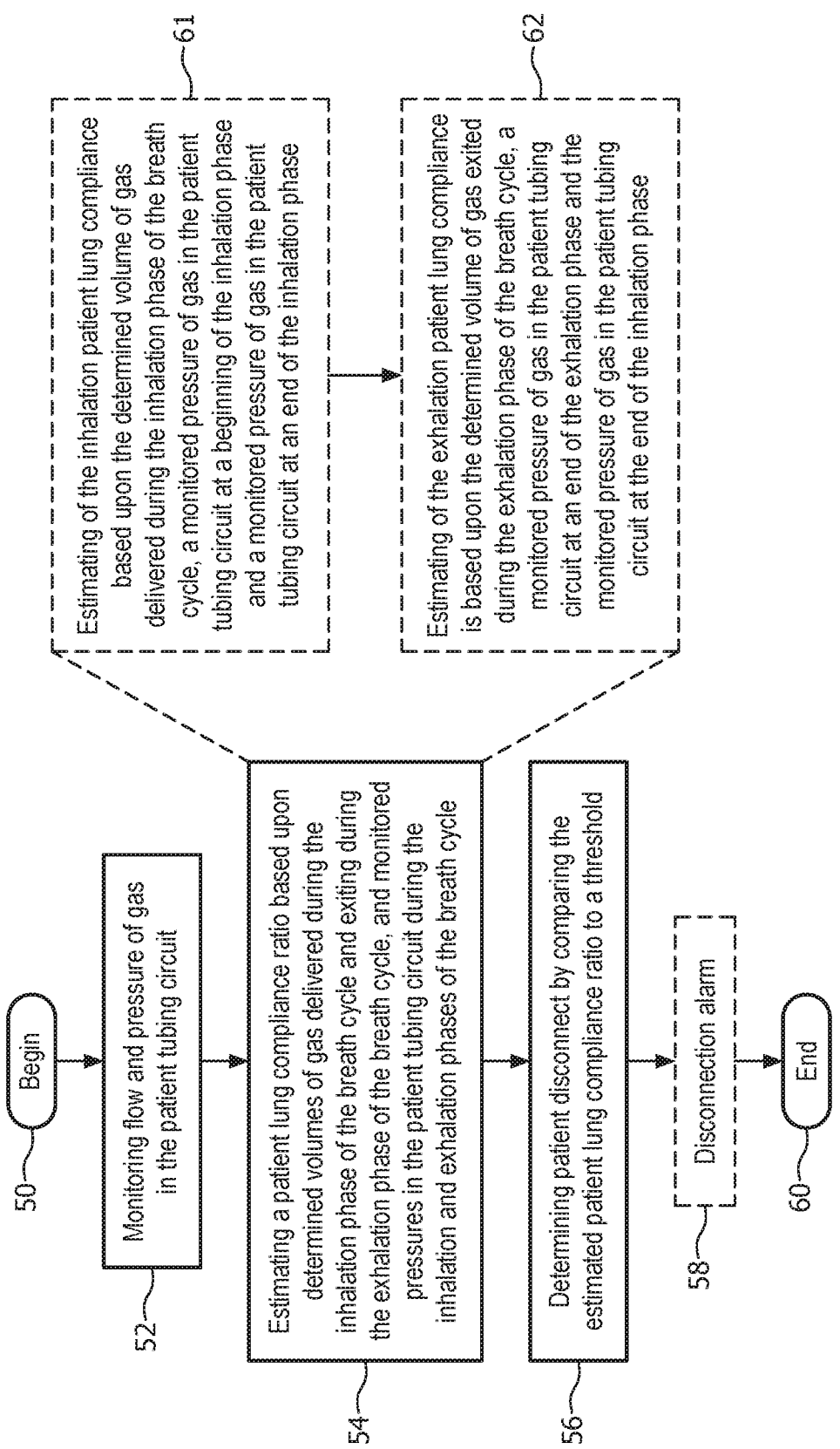
FIG. 2 is a flowchart illustrating various steps in a method of determining patient disconnection from a ventilation breathing system in accordance with features of an embodiment of the present invention.

Embodiments of the invention are also directed to a method of determining a patient disconnection from a ventilator breathing system (VBS) 10 configured to provide breathing gas to a patient via a patient tubing circuit 14 and having a breath cycle including an inhalation phase and an exhalation phase. An embodiment of the method will be described with additional reference to the flowchart of FIG. 2. The method begins 50 and includes: monitoring 52 at least flow and pressure of gas in the patient tubing circuit; estimating 54 a patient lung compliance ratio based upon determined volumes of gas delivered during the inhalation phase of the breath cycle and exiting during the exhalation phase of the breath cycle, and monitored pressures in the patient tubing circuit during the inhalation and exhalation phases of the breath cycle; and determining 56 patient disconnect by comparing the estimated patient lung compliance ratio to a threshold. An alarm may be triggered at block 58 as discussed above before the method ends 60.

In certain embodiments, estimating the patient lung compliance ratio comprises estimating 61 an inhalation patient lung compliance during the inhalation phase of the breath cycle, and estimating 62 an exhalation patient lung compliance during the exhalation phase of the breath cycle. The estimating 61 of the inhalation patient lung compliance is based upon the determined volume of gas delivered during the inhalation phase of the breath cycle, a monitored pressure of gas in the patient tubing circuit 14 at a beginning of the inhalation phase and a monitored pressure of gas in the patient tubing circuit 14 at an end of the inhalation phase. The estimating 62 of the exhalation patient lung compliance is based upon the determined volume of gas exited during the exhalation phase of the breath cycle, a monitored pressure of gas in the patient tubing circuit 14 at an end of the exhalation phase and the monitored pressure of gas in the patient tubing circuit 14 at the end of the inhalation phase.

More specifically, as discussed above, in certain embodiments of the method, estimating the patient lung compliance ratio includes estimating an inhalation patient lung compliance during the inhalation phase of the breath cycle, and estimating an exhalation patient lung compliance during the exhalation phase of the breath cycle; wherein the patient lung compliance ratio=$(C_{inh}/C_{exh})$; $C_{inh}$ is the inhalation patient lung compliance estimated during the inhalation phase and is calculated as $C_{inh}=V_{inh}/(P_{eoi}-P_{boi})$; $C_{exh}$ is the exhalation patient lung compliance estimated during the exhalation phase and is calculated as $C_{exh}=V_{exh}/(P_{eoi}-P_{eoe})$; wherein $V_{inh}$=the volume of gas delivered during the inhalation phase, $V_{exh}$=the volume of gas exiting during the exhalation phase, $P_{boi}$=pressure monitored in the patient tubing circuit 14 at the beginning of the inhalation phase, $P_{eoi}$=pressure monitored in the patient tubing circuit 14 at the end of the inhalation phase, $P_{eoe}$=pressure monitored in the patient tubing circuit at the end of the exhalation phase. It is noted that Vinh and Vexh are the result of integration of the flow to or out of the patient which can be either measured or estimated.

Embodiments of the invention may also be directed to a non-transitory computer-readable storage medium having stored therein machine readable instructions configured to be executed by a processor to control a ventilator breathing system (VBS) 10 to provide breathing gas to a patient via a patient tubing circuit 14 and having a breath cycle including an inhalation phase and an exhalation phase, the machine readable instructions being configured to cause the VBS 10 to execute a process to determine a patient disconnection from the VBS 10 including: monitoring at least flow and pressure of gas in the patient tubing circuit 14; estimating a patient lung compliance ratio based upon determined volumes of gas delivered during the inhalation phase of the breath cycle and exiting during the exhalation phase of the breath cycle, and monitored pressures in the patient tubing circuit 14 during the inhalation and exhalation phases of the breath cycle; and determining patient disconnect by comparing the estimated patient lung compliance ratio to a threshold.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer-readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

'Computer memory' or 'memory' is an example of a computer-readable storage medium. Computer memory is any memory which is directly accessible to a processor. Examples of computer memory include, but are not limited to: RAM memory, registers, and register files. References to 'computer memory' or 'memory' should be interpreted as possibly being multiple memories. The memory may for instance be multiple memories within the same computer system. The memory may also be multiple memories distributed amongst multiple computer systems or computing devices.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to 'computer storage' or 'storage' should be interpreted as possibly including multiple storage devices or components. For instance, the storage may include multiple storage devices within the same computer system or computing device. The storage may also include multiple storages distributed amongst multiple computer systems or computing devices.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a touch screen, keyboard, mouse, trackball, touchpad, pointing stick, graphics tablet, joystick, gamepad, webcam, headset, gear sticks, steering wheel, wired glove, wireless remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

What is claimed is:

1. A ventilator breathing system (VBS) to provide breathing gas to a patient, and having a breath cycle including an inhalation phase and an exhalation phase, the VBS comprising:
   a gas supply;
   a patient tubing circuit coupled to the gas supply;
   a gas monitoring system associated with the patient tubing circuit and configured to monitor at least flow and pressure; and
   a control unit coupled to the gas monitoring system and configured to determine a patient disconnection from the VBS by estimating a patient lung compliance ratio based upon determined volumes of gas delivered during the inhalation phase of the breath cycle and exiting during the exhalation phase of the breath cycle, and monitored pressures in the patient tubing circuit during the inhalation and exhalation phases of the breath cycle,
      wherein the control unit is configured to estimate the patient lung compliance ratio by estimating an inhalation patient lung compliance during the inhalation phase of the breath cycle, and estimating an exhalation patient lung compliance during the exhalation phase of the breath cycle, and dividing (1) the estimated inhalation patient lung compliance during the inhalation phase by (2) the estimated patient lung compliance during the exhalation phase; and
      wherein the control unit is configured to determine the patient disconnection from the VBS by comparing the ratio to a predetermined threshold value for the ratio alone, and responsive to determining the patient disconnection, cause an alarm.

2. The VBS of claim 1, wherein the patient tubing circuit includes a patient interface, an inspiratory branch and an expiratory branch each in fluid communication with each other via a tubing circuit wye; and wherein the gas monitoring system comprises a plurality of sensors including one or more inspiratory branch sensors and one or more expiratory branch sensors.

3. The VBS of claim 1, wherein the gas supply comprises a pump and a reservoir.

4. The VBS of claim 1, wherein the control unit is configured to estimate inhalation patient lung compliance based upon the determined volume of gas delivered during the inhalation phase of the breath cycle, a monitored pressure of gas in the patient tubing circuit at a beginning of the inhalation phase and a monitored pressure of gas in the patient tubing circuit at an end of the inhalation phase.

5. The VBS of claim 1, wherein the control unit is configured to estimate exhalation patient lung compliance based upon the determined volume of gas exited during the exhalation phase of the breath cycle, a monitored pressure of gas in the patient tubing circuit at an end of the exhalation phase and a monitored pressure of gas in the patient tubing circuit at the end of the inhalation phase.

6. The VBS of claim 1, wherein the control unit is configured to estimate the patient lung compliance ratio by estimating the inhalation patient lung compliance during the inhalation phase of the breath cycle, and estimating the exhalation patient lung compliance during the exhalation phase of the breath cycle; wherein the patient lung compliance ratio=$(C_{inh}/C_{exh})$; $C_{inh}$ is the inhalation patient lung compliance estimated during the inhalation phase and is calculated as $C_{inh}=V_{inh}/(P_{eoi}-P_{boi})$; $C_{exh}$ is the exhalation patient lung compliance estimated during the exhalation phase and is calculated as $C_{exh}=V_{exh}/(P_{eoi}-P_{eoe})$; wherein $V_{inh}$=the volume of gas delivered during the inhalation phase, $V_{exh}$=the volume of gas exiting during the exhalation phase, $P_{boi}$=pressure monitored in the patient tubing circuit at the beginning of the inhalation phase, $P_{eoi}$=pressure monitored in the patient tubing circuit at the end of the inhalation phase, $P_{eoe}$=pressure monitored in the patient tubing circuit at the end of the exhalation phase; and wherein the control unit is configured to determine the patient disconnection from the VBS by comparing the estimated patient lung compliance ratio to the value.

7. A non-transitory computer-readable storage medium having stored therein machine readable instructions configured to be executed by a processor to control a ventilator breathing system (VBS) to provide breathing gas to a patient via a patient tubing circuit and having a breath cycle including an inhalation phase and an exhalation phase, the machine readable instructions being configured to cause the VBS to execute a process to determine a patient disconnection from the VBS comprising:
   monitoring at least flow and pressure of gas in the patient tubing circuit;
   estimating a patient lung compliance ratio based upon determined volumes of gas delivered during the inhalation phase of the breath cycle and exiting during the exhalation phase of the breath cycle, and monitored pressures in the patient tubing circuit during the inhalation and exhalation phases of the breath cycle;
   determining patient disconnect by comparing the estimated patient lung compliance ratio to a predetermined threshold value for the estimated patient lung compliance ratio alone,
   wherein estimating the patient lung compliance ratio comprises estimating an inhalation patient lung compliance during the inhalation phase of the breath cycle, estimating an exhalation patient lung compliance during the exhalation phase of the breath cycle, and dividing (1) the estimated inhalation patient lung compliance during the inhalation phase by (2) the estimated patient lung compliance during the exhalation phase; and
   responsive to determining the patient disconnect, causing an alarm.

8. The non-transitory computer-readable storage medium of claim 7, wherein the patient tubing circuit includes a patient interface, an inspiratory branch and an expiratory branch each in fluid communication with each other via a tubing circuit wye; and wherein monitoring comprises processing signals from a plurality of sensors in the inspiratory branch and expiratory branch.

9. The non-transitory computer-readable storage medium of claim 7, wherein the estimating of the inhalation patient lung compliance is based upon the determined volume of gas delivered during the inhalation phase of the breath cycle, a monitored pressure of gas in the patient tubing circuit at a beginning of the inhalation phase and a monitored pressure of gas in the patient tubing circuit at an end of the inhalation phase.

10. The non-transitory computer-readable storage medium of claim 7, wherein the estimating of the exhalation patient lung compliance is based upon the determined volume of gas exited during the exhalation phase of the breath cycle, a monitored pressure of gas in the patient tubing circuit at an end of the exhalation phase and the monitored pressure of gas in the patient tubing circuit at the end of the inhalation phase.

11. The non-transitory computer-readable storage medium of claim 7, wherein estimating the patient lung compliance ratio comprises estimating the inhalation patient lung compliance during the inhalation phase of the breath cycle, and estimating the exhalation patient lung compliance during the exhalation phase of the breath cycle; wherein the patient lung compliance ratio=$(C_{inh}/C_{exh})$; $C_{inh}$ is the inhalation patient lung compliance estimated during the inhalation phase and is calculated as $C_{inh}=V_{inh}/(P_{eoi}-P_{boi})$; $C_{exh}$ is the exhalation patient lung compliance estimated during the exhalation phase and is calculated as $C_{exh}=V_{exh}/(P_{eoi}-P_{eoe})$; wherein $V_{inh}$=the volume of gas delivered during the inhalation phase, $V_{exh}$=the volume of gas exiting during the exhalation phase, $P_{boi}$=pressure monitored in the patient tubing circuit at the beginning of the inhalation phase, $P_{eoi}$=pressure monitored in the patient tubing circuit at the end of the inhalation phase, $P_{eoe}$=pressure monitored in the patient tubing circuit at the end of the exhalation phase.

12. The VBS of claim 1, wherein the control unit is configured such that the predetermined threshold value is indicative of a disconnection type.

13. The VBS of claim 1, wherein in the control unit is configured such that the predetermined threshold value is determined separate from (1) the estimated inhalation patient lung compliance during the inhalation phase and (2) the estimated patient lung compliance during the exhalation phase.

14. The non-transitory computer-readable storage medium of claim 7, wherein the predetermined threshold value is indicative of a disconnection type.

15. The non-transitory computer-readable storage medium of claim 7, wherein the predetermined threshold value is determined separate from (1) the estimated inhalation patient lung compliance during the inhalation phase and (2) the estimated patient lung compliance during the exhalation phase.

* * * * *